United States Patent
Deprez et al.

(10) Patent No.: US 9,786,401 B2
(45) Date of Patent: Oct. 10, 2017

(54) METHOD AND SYSTEM FOR COLLIMATING

(75) Inventors: Karel Deprez, Ghent (BE); Karen Van Audenhaege, Ghent (BE); Roel Van Holen, Ghent (BE); Stefaan Vandenberghe, Oosterzele (BE)

(73) Assignee: UNIVERSITEIT GENT, Ghent (BE)

( * ) Notice: Subject to any disclaimer, the term of this patent is extended or adjusted under 35 U.S.C. 154(b) by 111 days.

(21) Appl. No.: 14/115,494

(22) PCT Filed: May 9, 2012

(86) PCT No.: PCT/EP2012/058589
§ 371 (c)(1),
(2), (4) Date: Nov. 4, 2013

(87) PCT Pub. No.: WO2012/152851
PCT Pub. Date: Nov. 15, 2012

(65) Prior Publication Data
US 2014/0077095 A1  Mar. 20, 2014

(30) Foreign Application Priority Data
May 10, 2011 (EP) ..................................... 11165483

(51) Int. Cl.
*G21K 1/04* (2006.01)
*A61B 6/03* (2006.01)
(Continued)

(52) U.S. Cl.
CPC ................ *G21K 1/04* (2013.01); *A61B 6/037* (2013.01); *A61B 6/06* (2013.01); *G21K 1/025* (2013.01); *G21K 1/043* (2013.01)

(58) Field of Classification Search
CPC .. G01T 1/164; G01T 1/29; G21K 1/02; A61B 6/03
(Continued)

(56) References Cited

U.S. PATENT DOCUMENTS 3,115,580 A * 12/1963 Brewer .......................... 378/152
3,840,747 A * 10/1974 Macovski ...................... 250/369
(Continued)

OTHER PUBLICATIONS

Accorsi et al., "Analytic Determination of the Resolution-Equivalent Effective Diameter of a Pinhole Collimator", IEEE Trans. Med. Imag., 2004, p. 750-763, vol. 23, No. 6.
(Continued)

*Primary Examiner* — David Porta
*Assistant Examiner* — Blake Riddick
(74) *Attorney, Agent, or Firm* — Workman Nydegger

(57) ABSTRACT

A collimating system (100) for collimating radiation received under different angles for performing tomography is described. The collimating system (100) comprises a static collimator (110) comprising a plurality of collimating apertures (112), shutters (120) for separately and temporarily shutting at least two of said collimating apertures (112), wherein the shutters (120) having a shutting element (122) for blocking said at least two collimating apertures (112), and at least one collimating element (140) distinct from the shutting element (122) for collimating radiation passing through non-shut collimating apertures (112) in a direction so as to control overlap between radiation stemming from different non-shut collimating apertures (112). The invention also relates to an imaging system comprising such a collimating system, a method for collimating and a corresponding controller and software related products.

20 Claims, 9 Drawing Sheets

(51) Int. Cl.
*A61B 6/06* (2006.01)
*G21K 1/02* (2006.01)

(58) Field of Classification Search
USPC .......... 250/395, 363.06, 363.04, 363.1, 369
See application file for complete search history.

(56) References Cited

U.S. PATENT DOCUMENTS

| | | | |
|---|---|---|---|
| 4,165,462 A * | 8/1979 | Macovski et al. | ....... 250/363.04 |
| 4,190,773 A * | 2/1980 | Braden et al. | ................. 378/10 |
| 4,641,335 A * | 2/1987 | Hahn | ............................ 378/153 |
| 7,439,514 B1 | 10/2008 | Uribe et al. | |
| 2008/0078937 A1* | 4/2008 | Tsuchiya | ............... G01T 1/2928 250/366 |
| 2008/0116383 A1* | 5/2008 | Joung | ................... G01T 1/1641 250/363.1 |
| 2011/0178359 A1* | 7/2011 | Hirschman | ............ A61B 6/037 600/4 |
| 2012/0061581 A1* | 3/2012 | Hugg et al. | ................... 250/394 |

OTHER PUBLICATIONS

International Search Report for corresponding PCT Application No. PCT/EP2012/058589, mailed Jun. 27, 2012.
Kyba et al., "Timing Measurements from a TOF-PET Scanner Using Local PMT Triggering", IEEE Nuclear Science Symposium Conference Record, 2007, p. 4123-4128.
Mallard et al., "The Performance of a Gamma Camera for the Visualization of Radioactive Isotopes in vivo", Physics in Medicine and Biology, 1963, p. 165-182, vol. 8.
Paix, D., "Pinhole imaging of gamma rays", Phys. Med. Biol., 1967, p. 489-500, vol. 12, No. 4.

\* cited by examiner

METHOD AND SYSTEM FOR COLLIMATING

FIELD OF THE INVENTION

The invention relates to the field of nuclear imaging. More specifically, the present invention relates to a collimating system for use in nuclear imaging, such as for example a collimating system for tomography, a corresponding tomography system and a method of collimating.

BACKGROUND OF THE INVENTION

Single Photon Emission Computed Tomography (SPECT) is a biomedical imaging technique that is often used in nuclear medicine to image functional processes. The gamma camera detects photons that are emitted due to decay of the tracer that was injected in the patient. The camera measures projections at different angles, which can then be used to reconstruct a 3D image of the distribution of the labeled molecules in the patient.

An important part of a SPECT scanner is the collimator. The collimator is used to only transmit gamma rays with certain directions. Behind this collimator is a detector that converts the gamma ray in a measurable signal. Two main types of collimators are known, being the parallel-hole collimator and the pinhole collimator. Pinhole collimators are used to select gamma rays from a cone. The projection of a pinhole collimator on a flat detector is a circular or elliptical region.

The efficiency of a pinhole collimator is typically very low because the aperture of a pinhole needs to be small in order to have a good resolution. To increase the efficiency of a pinhole collimator, multiple pinholes can be placed on the same collimator. To maximize the number of pinholes, an optimal usage of the detector area is necessary. Typically, a tradeoff has to be made when using pinholes on rectangular detectors. The projections of the different pinholes will either overlap, or some valuable detector area will not be used.

Overlap is often undesirable because the detections in the regions of overlap will be more ambiguous. However, a combination of overlapping and non-overlapping data can improve the reconstruction quality.

In the case of a full-ring detector, a cylindrical multi-pinhole collimator is typically used. The number of pinholes on the collimator is restricted by the size of the detector, the radius of the collimator, the field-of-view and the amount of overlap allowed on the detector. This restriction can be a problem for data-completeness, e.g. when the restricted amount of pinholes is less than 60. When the field-of-view is small, the detector is very large and/or the radius of the collimator is also large, data-completeness might not be a problem. In order to successfully reconstruct a 3D image, we need projections under different angles. 60 projections are typically used in clinical practice.

SUMMARY OF THE INVENTION

It is an object of embodiments of the present invention to provide good methods and systems for collimating.

It is an advantage of embodiments according to the present invention that the collimator has no rotating parts and does not need to be rotated, as enough collimating apertures can be provided for obtaining data-completeness.

It is an advantage of embodiments of the present invention that data completeness can be obtained for tomography, without introducing large problems of overlap.

It is an advantage of embodiments of the present invention that overlapping projections can selectively be taken into account and that such a selection can be a dynamic selection, depending on the object to be imaged and the information to be obtained. It thus is an advantage of embodiments according to the present invention that the amount of overlap can be adjusted through different set-ups.

It is an advantage of embodiments according to the present invention that a more efficient use can be made of the available detector surface positioned after the collimator, compared to e.g. conventional pinhole systems.

It is an advantage of embodiments according to the present invention that the collimator can be made thinner, allowing more collimating apertures to be placed next to each other.

It is an advantage of embodiments according to the present invention that overlap between radiation stemming from different non-shut collimating apertures can be controlled more precisely and more efficient usage is made of the available detector area.

It is an advantage of the embodiments that one or more problems mentioned in the background can be reduced or solved.

It is an advantage of the embodiments of the present invention that the collimating system does not need to rotate. Collimators are made of heavy collimating material, like for example lead, tungsten or alloys of these materials. Rotating such a heavy collimator with a high precision is a technical challenge that can be avoided by embodiments of the present invention.

The above objective is accomplished by a method and device according to the present invention.

In one aspect, the present invention relates to a collimating system for collimating radiation received under different angles for performing tomography, the collimating system comprising a static collimator comprising a plurality of collimating apertures, shutters for selectively and temporarily shutting at least two of said collimating apertures wherein the shutters have a shutting element for closing the at least two collimating apertures, and at least one collimating element distinct from the shutting element for collimating radiation passing through non-shut collimating apertures in a direction so as to control overlap between radiation stemming from different non-shut collimating apertures. Selectively shutting may comprise or may be individually shutting collimating apertures or groups of collimating apertures. Selectively shutting apertures or groups of collimating apertures may be or may comprise selecting for each aperture or for each group of apertures to shut or not to shut it, and shutting or not shutting the collimating aperture or group of collimating apertures correspondingly. It is an advantage of embodiments according to the present invention that overlap of radiation stemming from different collimating holes can be controlled. It is an advantage of embodiments of the present invention that the amount of overlap may be adjusted through different set-ups or different types of applications.

The at least one collimating element may be provided for collimating radiation in axial direction, in transaxial direction or in a combination of both directions. Where in embodiments of the present invention reference is made to collimation in transaxial direction, reference is made to collimation in a plane perpendicular to the axial direction.

The collimating elements are distinct from the shutting elements. Where in embodiments of the present invention reference is made to collimating elements that are distinct from the shutting elements, reference is made to collimating elements that are functionally distinct from the shutting elements, i.e. whereby collimation does not occur by exclusively using the shutting elements.

The shutting element may have a thickness of at least 0.5 mm over its shutting area for blocking radiation passing through the collimating apertures. Where in embodiments of the present invention reference is made to the shutting area, reference is made to the area that needs to be blocked for preventing radiation passing through the collimating aperture to reach the detector. It is an advantage of embodiments according to the present invention that accurate shutting can be provided. It is an advantage of embodiments according to the present invention that sufficiently absorbing material can be provided for blocking radiation from the collimating hole, so that no erroneous detection is obtained and an appropriate background radiation level can be reached. In some embodiments, the thickness of the shutting element may be at least 0.5 mm or e.g. at least 1 mm or more.

The static collimator may be at least partially ring-shaped and the collimating apertures may be positioned on a same collimator ring. Embodiments of the present invention may be especially suitable for ring-shaped multi-aperture collimators, wherein currently often rotating collimators need to be used to avoid or reduce overlap resulting in disturbing interaction of the rotating system.

The at least one collimating element may be part of one of the shutters. The at least one collimating element and the shutting element may be fabricated from one block of material, forming one unitary element. In such an embodiment the at least one collimating element and shutting element are operated and controlled simultaneously. Moving shutting elements for closing at least two collimating apertures will then move the associated at least one collimating element for collimating radiation passing through certain non-shut collimating apertures to control overlap, for instance for collimating radiation passing through one or more neighbouring non-shut collimating apertures.

Non-static collimating elements, such as for instance simultaneously moving shutting elements and collimating elements, have the advantage that the degree of freedom for designing and positioning the collimating elements may be increased. If the degree of freedom for designing and positioning the collimating elements increases, the precision with which overlap can be controlled may be further increased.

The at least one collimating element and the shutting element may form two separate elements. In such an embodiment the at least one collimating element and corresponding shutting element may be operated and controlled simultaneously, meaning that moving shutting elements for closing at least two collimating apertures will move the associated at least one collimating element for collimating radiation passing through certain non-shut collimating apertures to control overlap, for instance for collimating radiation passing through one or more neighbouring non-shut collimating apertures. In such an embodiment the collimating elements and shutting elements may alternatively be operated and controlled independently from one another.

The at least one collimating element may be part of one of the shutters such that a shutter having a shutting element for shutting a predetermined collimating aperture comprises at least one collimating element shaped for controlling collimation of radiation passing through another collimating aperture. In some embodiments, the another collimating aperture may be a collimating aperture neighbouring the predetermined collimating aperture. It is an advantage of embodiments according to the present invention that the additional collimating can be easily introduced by adding a collimating element for collimating radiation from a given collimating hole to a shutter for shutting a neighbouring collimating hole. The latter avoids the need for introduction of an additional complete separate and further collimator. The at least one collimating element may comprise a slanted surface of the shutter.

The at least one collimating element may be part of an additional collimator configured with respect to the static collimator for controlling overlap between radiation stemming from different non-shut collimating apertures. It is an advantage of embodiments according to the present invention that the static collimator can also be used by a further collimating element, i.e. that it allows for configuring with other optional elements. The additional collimator may be a collimator ring providing collimation in a direction determining overlap between radiation stemming from different non-shut collimating holes. The at least one collimating element may comprise radiation transparent windows in the additional collimator made of absorbing material. The at last one collimating element may be a non-static element, meaning that it is movable with respect to the at least one collimating aperture.

The at least one collimating element and the shutting element may be operated and controlled simultaneously or independently from one another.

The at least one collimating element may be a movable element with respect to the collimating apertures. The movement may be for example by a pneumatic, hydraulic or electric actuator, embodiments of the present invention not being limited thereto. For blocking, shutters may for example be moved in front of a collimating aperture or away from the collimating aperture, e.g. by shifting, translating, rotating, . . . . The movement may be performed for example by a pneumatic, hydraulic or electric actuator embodiments of the present invention not being limited thereto.

At least one of the shutters or shutting elements, a subset of the shutters or shutting elements, or each of the shutters or shutting elements may be individually controllable. Individually controllable shutters or shutting elements may allow for each aperture or for each group of apertures to shut or not to shut it. Individually controllable shutters or shutting elements or subsets of shutters or shutting elements may allow shutting at least two of said collimating apertures independently from one another.

The at least one collimating element, a subset of the collimating elements, or each of the collimating elements may be individually controllable.

The collimating system may comprise a controller programmed for controlling the shutters for opening the collimating apertures in a predetermined manner. It is an advantage of embodiments according to the present invention that shutting of collimating holes can be performed in an automated way, without the need for human interaction, e.g. without the need for human interaction during measurements.

The controller may be programmed for alternatingly and temporarily opening the shutting elements for collimating apertures, e.g. non-neighbouring collimating apertures. It is an advantage of embodiments according to the present invention that separate shutting control of collimating holes can be obtained, allowing simultaneous use of apertures that are sufficiently far distantiated from each other and collimated to avoid or limit overlap of the radiation to be detected.

The controller may be programmed for individually controlling a subset or each of the shutters and or shutting elements allowing for closing at any time any of the plurality of collimating apertures. The controller may be programmed for individually controlling a subset or each of the at least one collimating element.

The controller may be programmed for alternatingly and temporarily opening shutting elements for a subset of collimating apertures such that over a predetermined time period, all collimating apertures have been un-shut. It is an advantage of embodiments according to the present invention that embodiments of the present invention for example allow emulating a rotational collimator using a static collimator. The latter allows for example to replace a rotational collimator with a limited number of apertures, whereby avoiding rotation of a collimator provides detecting data in a less disturbed measurement environment. For example, the electromagnetic influences of a motor for rotating the collimator can be avoided.

The static collimator may be at least partially ring-shaped. Embodiments of the present invention may be especially suitable for ring-shaped multi-aperture collimators, wherein currently often rotating collimators need to be used to avoid or reduce overlap resulting in disturbing interaction of the rotating system.

The number of apertures may be at least 15, e.g. at least 24. The number of apertures may be at least 30, e.g. at least 45, e.g. at least 60. It is an advantage of embodiments according to the present invention that the number of collimating apertures is not strongly restricted by the field-of-view of the system, as the collimating apertures can be shut alternatingly and therefore do not need to be used simultaneously.

The static collimator may be ring shaped and may be for use with a ring shaped detector and the number of apertures may fulfill the following equation $$\text{number of apertures} > \frac{\pi}{\text{acos}\left(\frac{R_{FOV}}{R_d}\right) - a\cos\left(\frac{R_{FOV}}{R_c}\right)}$$

wherein $R_d$ is the radius of the detector, $R_c$ is the radius of the static collimator and $R_{FOV}$ is the transaxional field-of-view The present invention also relates to an imaging system comprising a detector, a collimating system as described above, and a correlator for correlating signals detected using the detector with collimated apertures un-shut at the moment of detection. The imaging system may be a biomedical imaging system. The imaging system may be a system for performing tomography. The imaging system may be a single photon emission computed tomography system.

The present invention also relates to a method for imaging an object, the method comprising selectively and temporarily shutting at least two of a plurality of collimating apertures of a static collimator using shutters having a shutting element for closing the collimating apertures thereby alternatingly and temporarily opening shutting elements for collimating apertures or subsets of collimating apertures, detecting the radiation transmitted through the un-shut collimating apertures, correlating the detected radiation with the collimator apertures un-shut during the detecting, and deriving therefrom information of the object of interest. Alternatingly and temporarily opening shutting elements for collimating apertures may be alternatingly and temporarily opening shutting elements for non-neighbouring collimating apertures.

The alternatingly and temporarily opening shutter elements may be such that a rotation of the static collimator is emulated.

Separately and temporarily shutting shutters may be separately and temporarily shutting shutters having a shutter element, the shutting element having a thickness of at least 0.5 mm over its shutting area for blocking radiation stemming from an object of interest passing through the collimating apertures.

The method may comprise using collimating elements, optionally collimating elements that are distinct from the shutting elements, for collimating radiation passing through non-shut collimating apertures in a direction so as to control overlap between radiation stemming from different non-shut collimating apertures.

In one aspect, the present invention relates to a collimating system for collimating radiation received under different angles for performing tomography, the collimating system comprising a static collimator comprising a plurality of collimating apertures, shutters for separately and temporarily shutting at least two of said collimating apertures, wherein the shutters having a shutting element for closing the at least two collimating apertures, and a controller for alternatingly and temporarily opening shutting elements for non-neighbouring collimating apertures. The collimating system may comprise a correlator for correlating detected radiation with the collimator apertures un-shut during the detecting, and further optionally for deriving therefrom information of the object of interest.

The present invention also relates to a controller for controlling a collimating system comprising a plurality of collimating apertures and shutter elements according to a method as described above.

The present invention further relates to a computer program product for, if implemented on a processing unit, performing a method as described above. The invention also relates to a data carrier storing the computer program product and the transmission of the computer program product over a network.

In one aspect, the present invention also relates to a collimating system for collimating radiation received under different angles for performing tomography, the collimating system comprising, a static collimator comprising a plurality of collimating apertures, shutters for separately and temporarily shutting at least two of said collimating pinholes, wherein the shutters having a shutting element for closing said at least two collimating pinholes, the shutting element having a thickness of at least 0.5 mm over its shutting area for blocking radiation passing through the collimating pinholes.

Particular and preferred aspects of the invention are set out in the accompanying independent and dependent claims. Features from the dependent claims may be combined with features of the independent claims and with features of other dependent claims as appropriate and not merely as explicitly set out in the claims. These and other aspects of the invention will be apparent from and elucidated with reference to the embodiment(s) described hereinafter.

Figure 1:
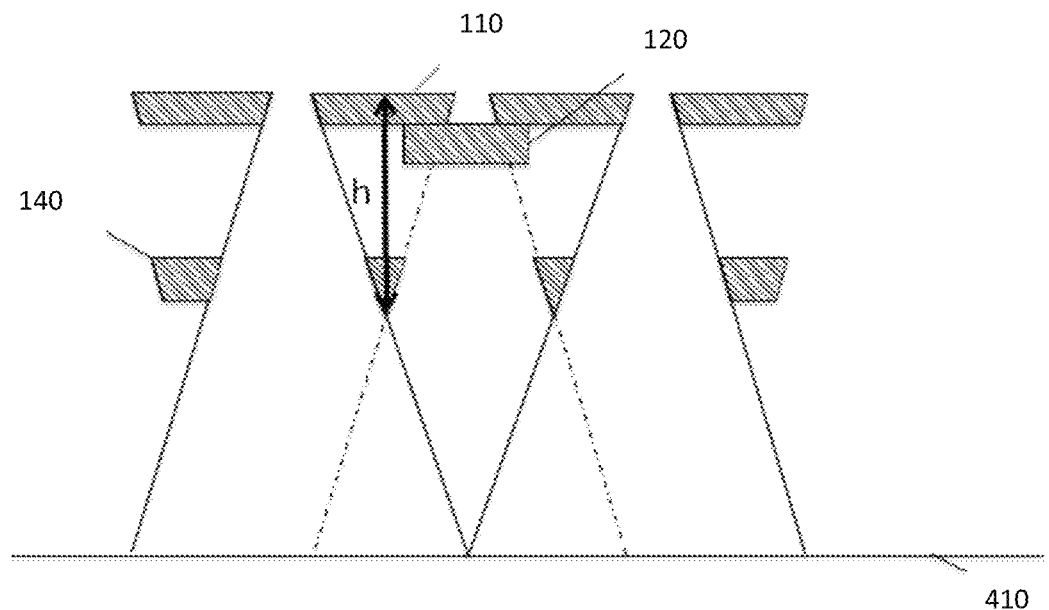
FIG. 1 is a schematic representation of a collimating system comprising controllable shutters and a collimating element, according to an embodiment of the present invention.

The drawings are only schematic and are non-limiting. In the drawings, the size of some of the elements may be exaggerated and not drawn on scale for illustrative purposes.

Any reference signs in the claims shall not be construed as limiting the scope. In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Where in embodiments of the present invention reference is made to an open shutter or an open or un-shut collimating aperture, reference is made to a state of the shutter, e.g. associated with the collimating aperture, such that at least some radiation passing the collimating aperture is able to reach the detector. The shutter may for example be shifted, rotated or more generally moved away from the aperture so that it is not blocking radiation.

Where in embodiments of the present invention reference is made to a closed shutter or to a closed or shut collimating aperture, reference is made to a state of the shutter, e.g. associated with the collimating aperture, such that the majority and preferably substantially all radiation passing the collimating aperture is blocked by the shutter so that it does not reach the detector.

Where in embodiments according to the present invention reference is made to radiation, reference may be made to electromagnetic radiation comprising amongst others gamma radiation, embodiments of the present invention not being limited thereto. For example a collimator according to embodiments of the present invention also can collimate electro-magnetic waves such as for example infrared radiation, visible radiation, UV radiation, X-rays.

In a first aspect, the present invention relates to a collimating system for collimating radiation received under different angles for performing tomography. Embodiments of the present invention may be especially suitable for performing single photon emission computed tomography, although embodiments of the present invention are not limited thereto. The collimating system according to embodiments of the present invention comprises a static collimator having a plurality of collimating apertures. Such apertures may be pinholes, but also may be alternative apertures such as slats, slits, particularly shaped pinholes, etc. The collimating system according to embodiments of the present invention also comprises shutters for selectively and temporarily shutting at least two of the collimating apertures. In embodiments of the present invention, the number of collimating apertures may typically be significantly larger than would be allowed for avoiding overlap during simultaneous use. The shutters according to embodiments of the present invention have a shutting element for closing the collimating aperture. Such a shutting element thus typically allows blocking radiation passing through a collimating aperture. According to embodiments of the present invention, the collimating system also comprises at least one collimating element for collimating radiation passing through non-shut collimating apertures in a direction so as to control overlap between radiation stemming from different non-shut collimating apertures.

By way of illustration, embodiments of the present invention not being limited thereto, further features and advantages will be described with reference to an exemplary system as shown in FIG. 1 to FIG. 6, comprising standard and optional features.

Figure 2:
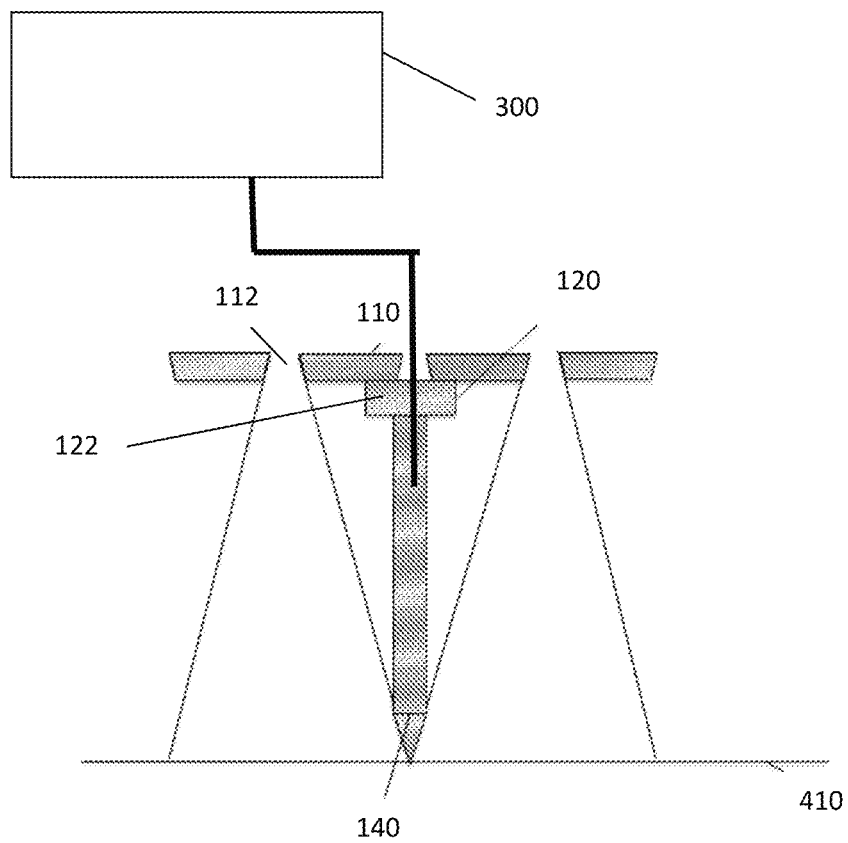
FIG. 2 is a schematic representation of another collimating system comprising controllable shutters and a collimating element, according to an embodiment of the present invention.

FIG. 1 and FIG. 2 illustrate a collimating system 100 comprising a static collimator 110. The static collimator 110 is adapted for collimating radiation from different angles, without the need for rotating during operation. For example, with reference to FIG. 2, it can be seen that by alternatingly shutting different apertures 112, radiation from different apertures is allowed to pass and optionally be further collimated by collimating elements 140. It also can be seen that the collimating element, placed on the shutter 120 in FIG. 2 can be placed further away from the collimator. It will not block radiation from the middle aperture when that one is open because the collimating will then also be moved away, together with the shutter. The static collimator 110 may at least be partially ring-shaped and the collimating apertures may be positioned on the same collimator ring. The static collimator alternatively also may have a different shape, such as a sphere, a polyhedron, a cube, . . . . The static collimator 110 comprises a plurality of collimating apertures 112. The collimating apertures may for example be pinholes. Alternatively, the collimating apertures may be slats, slits, particularly shaped pinholes, etc. The number of collimating apertures that can be introduced therefore can be at least 16, at least 32, at least 64, at least 128 and may be at the upper side limited by the physical place required by the collimating apertures on the collimator. In embodiments of the present invention, the number of collimating apertures may typically be significantly larger than would be allowed for avoiding overlap during simultaneous use. Shutters may be provided on one, more or each of the collimating apertures. In other words it is an advantage of embodiments according to the present invention that the number of collimating apertures can be so large that neighbouring pinholes have overlapping projections, as the use of shutters allows closing the collimating apertures so that, if not desired, overlap on the detector can be avoided and the detections can be performed separately, e.g. shifted in time.

In a ring shaped embodiment for example, i.e. when the collimating system is ring shaped and with the detector to be used also ring shaped, the number of collimating elements which would be an upper limit in an unshut prior art system for avoiding overlap and which may be larger due to the shutting possibility in embodiments of the present invention, can be calculated as following: Given a detector radius (Rd), a collimator radius (Rc), a transaxional FOV Radius (RFOV) (indicated in FIG. 7—left part, by way of illustration) and given the fact that no overlap is allowed, then the number of apertures on one ring on the collimator is normally limited to $$x = \frac{\pi}{\acos\left(\frac{R_{FOV}}{R_d}\right) - a\cos\left(\frac{R_{FOV}}{R_c}\right)}$$

wherein $R_d$ is the radius of the detector, $R_c$ is the radius of the static collimator (110) and $R_{FOV}$ is the transaxional field-of-view radius.

When the collimating shutters described in this invention are used, the number of apertures that can be placed on one ring on the collimator is not limited to this formula any more.

Similarly, also the maximum height of a further static collimating element 140 for collimating with respect to the collimator and its collimating apertures in a prior art system can be calculated: Given a detector radius (Rd), a collimator radius (Rc), a transaxional FOV Radius (RFOV), a collimator ring with x apertures and given the fact that no overlap is allowed, the height at which a collimating element can normally be placed is expressed as $$h = \frac{R_c \cdot \tan\left(\frac{\pi}{x}\right)}{\tan\left(a\sin\left(\frac{R_{FOV}}{R_c}\right) - \tan\left(\frac{\pi}{x}\right)\right)}$$

with h the height of the collimating element above the collimator (towards the detector), as also indicated in FIG. 1 and FIG. 2. More particularly, in FIG. 1, it can be seen that the maximum distance at which a collimating element can be placed when it is static is at a distance h from the static collimator 110. Placing the collimating element 140 further away would block radiation from the middle apertures when it would be open (as the collimating elements in this configuration are static and do not shift together with the shutters). Alternatively, the collimating elements 140 in such a configuration could also be made moveable. With the shutting design according to embodiments of the present invention, this height can be increased further, while still allowing to obtain no overlap. Collimating further away from the aperture gives a sharper projection.

The static collimator 110 typically is made of a material that is substantially blocking the radiation, except at areas where collimating apertures are present. Such material may be particularly selected as function of the radiation used in the application. Typical materials that may be used are for example tungsten, lead, platinum or gold or alloys of these materials.

The static collimator 110 according to embodiments of the present invention is such that no rotation of the collimator itself is required, while providing sufficient collimating apertures so that data completeness is obtained.

Figure 3:
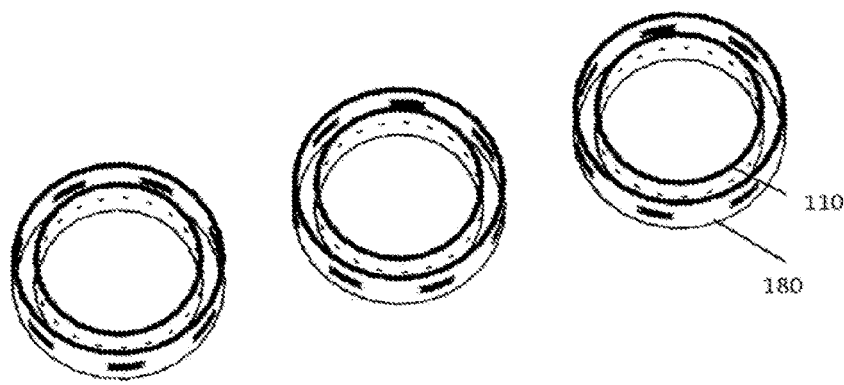
FIG. 3 is an example of part of a collimating system comprising a shutter ring for controlling shutting of collimating apertures, according to an embodiment of the present invention.
Figure 16:
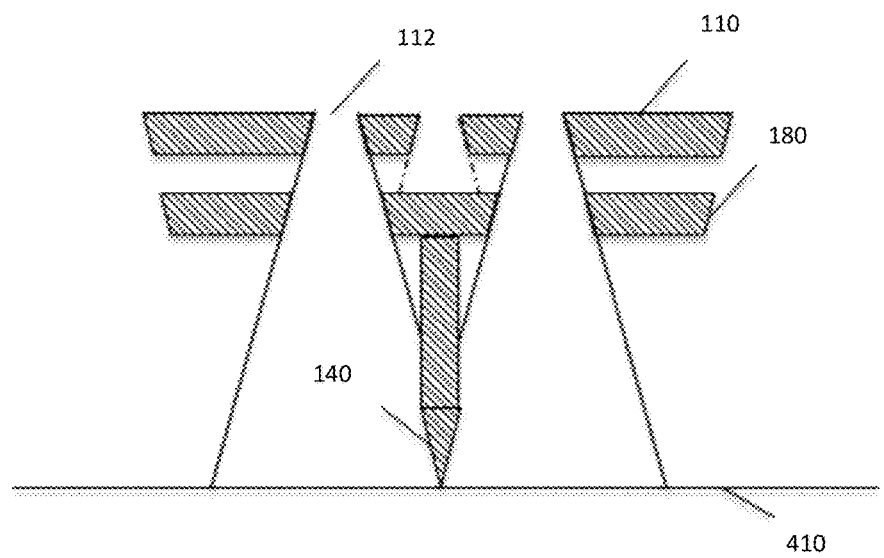
FIG. 16 is a schematic view of part of a collimating system comprising a shutter ring for controlling shutting of collimating apertures, according to an embodiment of the present invention.

According to embodiments of the present invention, at least two shutters 120 are present comprising a shutting element 122 for separately and temporarily shutting at least two of the collimating apertures. The shutters according to embodiments of the present invention have a shutting element for closing one of the at least two of the collimating apertures. The shutter element may be any type of shutter. The shutter element advantageously has a thickness such that it can block radiation passing through the collimating hole. The shutter element therefore advantageously is made of a material having sufficient stopping potential for the radiation used, e.g. for gamma-radiation. The material forming the shutting element may advantageously be a high-density material. The thickness of the shutter elements may be at least 0.5 mm, e.g. at least 1 mm over the full area where they shut of the radiation. The thickness may be determined as function of the radiation that will be used for e.g. a SPECT system and may be such that less than 1%, advantageously less than 0.1%, still more advantageously less than 0.01% radiation is transmitted. The required thickness may be determined based on the required attenuation factor to be obtained. The attenuation factor is given by $\rho = e^{-\mu(E)l}$ with l the thickness of the shutting element and $\mu(E)$ the attenuation coefficient of the shutter material at a certain energy E. E.g. using an isotope Tc-99m with an energy 140 keV, a thickness of tungsten shutting elements of 5 mm allows blocking at least 81.99% of the radiation. Using e.g. 1-125 with an energy of 30 keV, a thickness of a lead shutting elements of 0.1 mm allows blocking at least 96.24%. The shutter element 122 may in some embodiments be made of blocking material, such as for example tungsten, lead, platinum or gold or alloys of these materials. For blocking, shutters may for example be moved in front of a collimating aperture or away from the collimating aperture, e.g. by shifting, translating, rotating, . . . . The movement may be performed for example by a pneumatic, hydraulic or electric actuator embodiments of the present invention not being limited thereto. The shutters may be controlled individually or may be controlled in group. In one embodiment, as shown in FIG. 3, the shutters may be provided as a shuttering ring. The system shown in FIG. 3 and in more detail in FIG. 16 illustrates a static collimator 110 with 21 collimating apertures and a shuttering ring 180 comprising 7 shutters, being windows in the shuttering ring. Rotation of the shuttering ring 180 results in shutting 14 collimating apertures and simultaneously selecting 7 collimating apertures. The shuttering ring 180 allows separately shutting some collimating apertures while opening shutters for other collimating apertures. The shuttering ring 180 thus allows separately shutting some apertures while opening other apertures.

Figure 4:
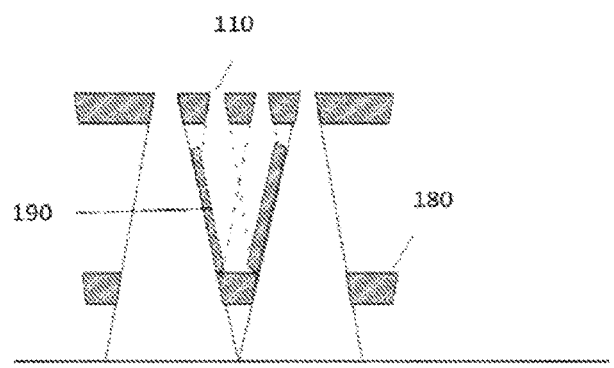
FIG. 4 is a schematic view of part of a collimating system comprising a shutter ring for controlling shutting of collimating apertures, according to an embodiment of the present invention.
Figure 5:
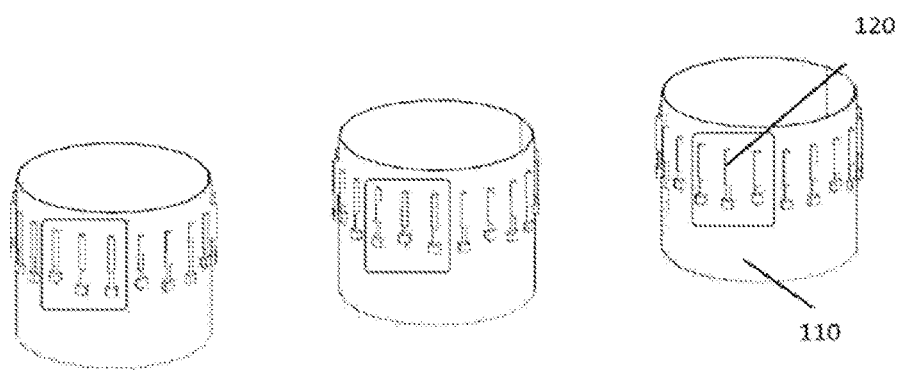
FIG. 5 is an example of part of a collimating system comprising controllable shutters, according to an embodiment of the present invention.

According to the embodiment shown in FIG. 3 and FIG. 16, the shutters thus are implemented as a rotating ring of windows, closing or opening certain apertures. The collimating system further comprises collimating elements 140 for collimating radiation passing through non-shut collimating apertures so as to control overlap between radiation stemming from different non-shut collimating apertures. In another embodiment, as shown in FIG. 4, the shuttering ring 180 comprises collimating elements 190 for collimating radiation passing through non-shut collimating apertures so as to control overlap between radiation stemming from different non-shut collimating apertures. In this embodiment the collimating elements 190 may have an additional shutting function as using only the shutter ring 180 would not be sufficient in the example shown because the rays of the middle apertures shown in FIG. 4 would also pass through the window of the neighbouring apertures. FIG. 3 and FIG. 4 thus illustrate shutters that may be controlled simultaneously or in group. In another embodiment, individual control of the different apertures is provided by individually controlling the shutters 120. Some or all of the collimating elements 190 and the shutting elements 180 may be operated independently from each other or simultaneously. In other words, the shutters may be adapted for shutting at least two of said collimating apertures independently. An example thereof is shown in FIG. 5, whereby the individually controllable shutters 120 are illustrated.

According to embodiments of the present invention, the collimating system also comprises at least one collimating element 140 for collimating radiation passing through non-shut collimating apertures 112 in a direction so as to control overlap between radiation stemming from different non-shut collimating apertures 112. The at least one collimating element is distinct from the shutting element, meaning that the collimation is not done exclusively by the shutting element. The collimating elements may take any possible shape. The collimating elements may have a slanted edge, rounded edge, may be pyramidal shaped, knive shaped, spherically shaped, etc. They advantageously may be made of high-density material. The collimating elements 140 have the function of collimating radiation, e.g. collimating gamma radiation. According to some embodiments of the present invention, the collimating elements may be introduced as separate collimating elements, not being part of the shutter. Alternatively, the collimating elements may be introduced as part of the shutters. In one embodiment, the at least one collimating element 140 may be part of the shutter 120, such that the shutter 120 having a shutting element 122 for shutting a predetermined collimating aperture 112, comprises the at least one collimating element 140 shaped for controlling collimation of radiation passing through a collimating aperture 112 neighbouring the predetermined collimating aperture 112. In embodiments of the present invention, at least one collimating element 140 may be present, a collimating element 140 may be present for some of the collimating apertures 112 or one or more collimating elements 140 may be present for each of the collimating apertures 112. By way of illustration, FIG. 5 and also FIG.

2 illustrate part of a collimating system comprising a shutter with a shutter element and a collimating element. In the particular example shown in FIG. 2, the collimating element is placed on top of the shutter. It acts as a knife, separating the circular projections. The collimating shutters in the present example are used in such a way that no two neighbouring apertures are open simultaneously, allowing separation through the collimating element of the projections obtained.

In contrast or in addition to distinct collimating elements being present in the shutter, in some embodiments, the shutters also may perform an additional collimating function by partially opening the shutter elements. In other words, the shutting elements also may perform an additional collimating function.

Figure 6:
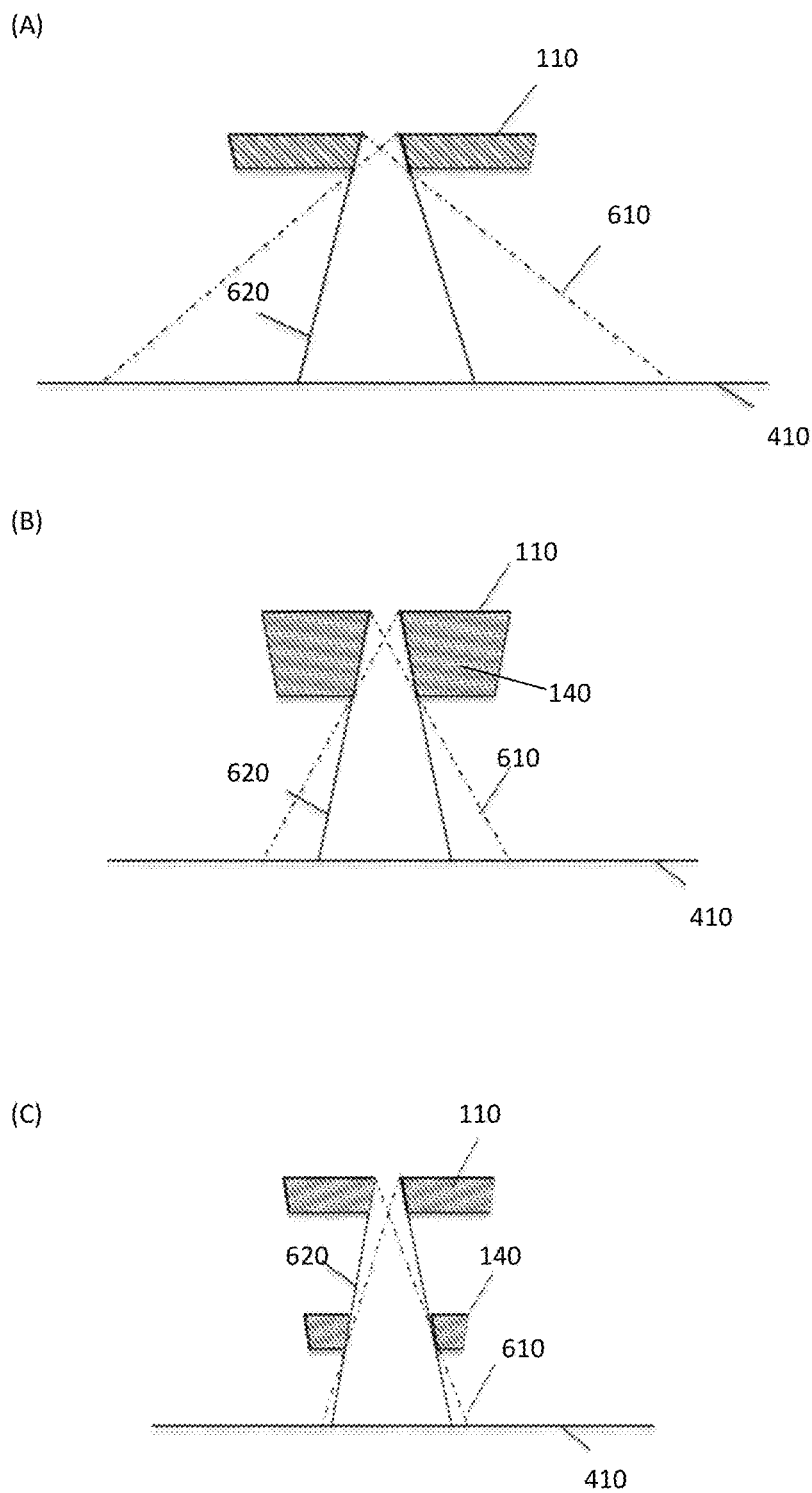
FIG. 6 (A), (B), (C) is a schematic illustration of the effect of the position of collimating elements on the projection, as can be used in embodiments of the present invention.

It is an advantage of the embodiments of the present invention that the blurry edge of the projections is very limited because the cut-off can happen at a relatively large distance from the pinholes. The occurrence of the blurry edge can be best explained using FIG. 6, illustrating one example wherein no further collimation is present (A), one example where the further collimation is performed close to or at the static collimator (B) and one example where the further collimation is performed at a distance from the static collimator. From FIG. 6 it can be seen that it is advantageous to have the additional collimation by the collimating elements as far as possible away from the static collimator 110 as the blurry projection then is smallest. In the different drawings, the blurry projection is indicated by reference numeral 610, whereas the sharp projection is given by reference numeral 620. The collimator thickness can then be very low. This is an advantage because of the high cost and weight of collimator material. When overlap is used, a low collimator thickness is also an advantage because the pinholes might otherwise start to intersect, which cannot be allowed for a correct functioning of the collimator.

The advantage of using shutters having a collimating element for collimating can for example be understood from the following. The projection of a pinhole is a circle or an ellipse and typically a tradeoff is to be made between allowing overlap of radiation from different apertures and not using some valuable detector area. Rectangular projections would solve this problem, but a number of solutions providing such rectangular projections induces further problems: the use of slats for predetermined collimating apertures of the collimator for separating the different projections can block projections from neighbouring collimating apertures. A similar disadvantage can be obtained when using collimating windows in combination with the collimator. As indicated, a rotating collimating wheel with collimating windows may be used, but has the disadvantage that there is the technical burden of rotating the rather heavy collimating wheel. Another way to achieve rectangular projections is to use loftholes instead of pinholes. Loftholes are collimator holes that have a volume that differs from a conical shape. By adapting the shape of the collimator hole, the projection shape can be adapted. Lofthole projections, however, have a blurry edge. To reduce the edge, one can increase the collimator thickness or decrease the aperture size. Decreasing the aperture size also lowers the sensitivity of the system. Increasing the collimator thickness will increase the weight and the price of the collimator, since the collimator is typically made of heavy and expensive materials. In accordance with at least some embodiments of the present invention, introducing collimating elements on one or more shutters results in a good separation of the projections. A collimating element mounted on a closed shutter serves as a cut-off system for both its neighboring pinholes. When the shutter is opened, the two neighboring shutters are closed and they serve as a cut-off system for the pinhole that is open. Introduction of the collimating element on the shutter therefore may overcome the problem of closing neighbouring collimating apertures while still having the advantage that the detector area can be more efficiently used due to the rectangular projections.

According to embodiments of the present invention, the collimating system 100 furthermore advantageously may comprise a controller 300, as shown in FIG. 2. Such a controller may be programmed for controlling the shutters for opening the collimating apertures in a predetermined manner Such a controller may be hardware or software based. The controller may be programmed so that shutting may be performed in an automatic and/or automated way, i.e. optionally without the need for human interaction. It is to be noticed that in alternative embodiments, control of the shutters may be performed manually or by human intervention. The controller 300 may be programmed for alternatingly and temporarily opening the shutting elements for non-neighbouring collimating apertures 112. By controlling the shutting of collimating holes, simultaneous use of apertures that are sufficiently far distantiated from each other and collimated is obtained allowing avoiding or limiting overlap of the radiation to be detected. In some embodiments, the controller 300 is programmed for alternatingly and temporarily opening shutting elements 122 for a subset of collimating apertures 112 such that over a predetermined time period, all collimating apertures 112 have been temporarily un-shut.

In one example, a virtual rotation of the collimator can be emulated by accurately shutting the collimating apertures. It is known that in order to be able to reconstruct the projection data to a 3D image, the imaged object should be recorded from a minimum of angles (typically 60 angles are used in clinical practice). According to prior art, the number of collimator apertures is limited by the amount of overlap allowed. For a large number of configurations, the number of collimating apertures allowed by the amount of overlap typically is not enough for data-completeness. According to a prior art solution, a limited number of collimating apertures is used and the collimator or the detector is rotated. This movement, which introduces a number of difficulties due to the weight of the components and in view of stability of the measurements, can be overcome in embodiments of the present invention by emulating the rotation. According to embodiments of the present invention, a virtual rotation may be emulated by alternatingly shutting different collimating apertures, avoiding the need for rotating the collimator and thus resulting in more stable and accurate measurements. For example, no disturbing effects of a motor required for rotating the collimator are present. In case of small field-of-view applications, such a shutting collimating technique can allow good imaging, even without the need for further collimating elements. For larger field-of-view shutters with collimating elements according to at least some embodiments of the present invention provide a good solution for accurate measurements.

In accordance with embodiments of the present techniques, it thus is possible to use a succession of shutter configurations to register the necessary projections under different angles without needing rotation and without affecting the amount of overlap. In other words, by opening the shutters in a predetermined manner, emulation of a virtual rotation of a collimator ring with limited number of collimating apertures can be obtained, allowing for example replacing a rotational collimator with limited number of apertures and thus avoiding rotation of a collimator resulting in a less disturbed measurement environment.

Figure 7:
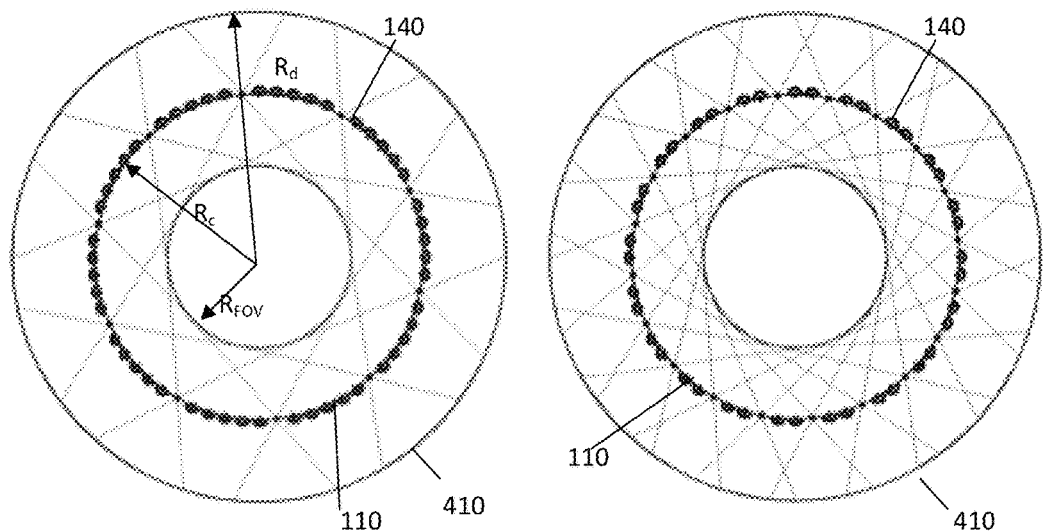
FIG. 7 illustrates an example of two different states of the shutter configuration, indicating the occurrence of more or less overlap between radiation of different collimating apertures, as can be used in embodiments of the present invention.

In accordance with embodiments of the present invention, the system may be adapted for adjusting the amount of overlap on the detector, by controlling the shutters or in other words by controlling which apertures are opened. In other words, the overlap can be used as a parameter. The overlap on the detector of radiation stemming from different collimating apertures may be chosen to be zero or non existing, thus allowing to make sure for each detected photon through which aperture it was directed, or it may be chosen to have some overlap, of which the amount can be chosen, to optimize the amount of radiation captured. It is an advantage of the embodiments of the present techniques that the amount of overlap can be adjusted. The shutters are configurable, so one can first do a scan without overlap and then do another scan with overlap. This can improve the reconstructed image quality. By way of illustration, an exemplary multi-pinhole collimator is shown in FIG. 7. In the left part of the figure, the shutters are configured such that there is no overlap. In the right part of the figure, another shutter configuration is used. More shutters are opened and there is a small amount of overlap. In some embodiments, the control of the shutters may be performed by the controller or in other words, the controller can be programmed so that a predetermined amount of overlap is obtained, optionally variable over time.

Whereas in the present aspect the collimating system is described as being characterized by the shutters and the at least one collimating element, it is to be understood that the present invention in some embodiments alternatively also relates to a collimating system as described above, wherein no additional collimating element is present, but which is characterized by the presence of shutters for separately and temporarily shutting collimating apertures. Optionally also a controller for alternatingly and temporarily opening shutting elements for non-neighbouring collimating apertures may be present. Such a controller then can also be further characterised in that through control of the shutters in a predetermined manner, it allows for emulating a virtual rotation of the collimating system.

Figure 8:
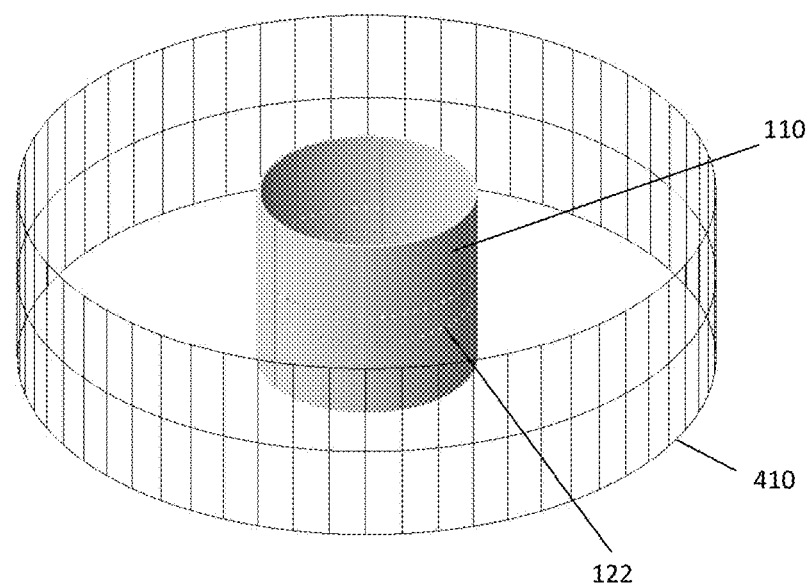
FIG. 8 illustrates a full-ring detector with a cylindrical collimator, being an example of part of an imaging system according to an embodiment of the present invention.

In one aspect, the present invention also relates to an imaging system for tomography using a collimating system as described above. Such an imaging system, which may for example be a SPECT imaging system, although embodiments of the present invention are not limited thereto, comprises a collimating systems as described in the first aspect or in an embodiment thereof, a detector element, and a correlator or correlating means for correlating, at different moments in time, signals detected using the detector with a set of collimated apertures un-shut at the moment of detection. The system may be a bio-imaging system. By way of illustration, embodiments of the present invention not being limited thereto, an example of an imaging system is discussed with reference to FIG. 8 to FIG. 10, indicating standard and optional features. FIG. 8 is a schematic illustration of an exemplary imaging system 400, in the present example being a SPECT system, which includes a collimator assembly, also referred to as collimating system 100, and a detector 410 assembly. The detector 410 in the present example is a full ring gamma detector, radiated using a cylindrical collimator 110 comprising a plurality of pinholes 112. The radius of the collimator 110 will typically be as small as possible because the sensitivity of a pinhole 112 decreases when the distance to the imaged object increases. Also, the geometric resolution of a pinhole collimator increases when the distance to the imaged object increases. Therefor, the radius of the collimator will typically be fixed and as small as possible.

Figure 9:
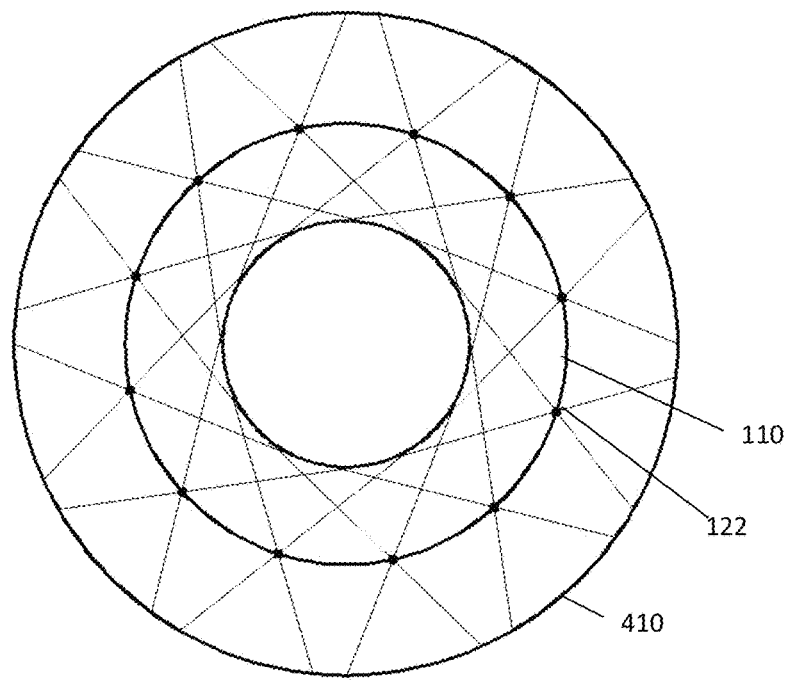
FIG. 9 illustrates a collimating aperture configuration wherein no overlap is present on the detector.
Figure 10:
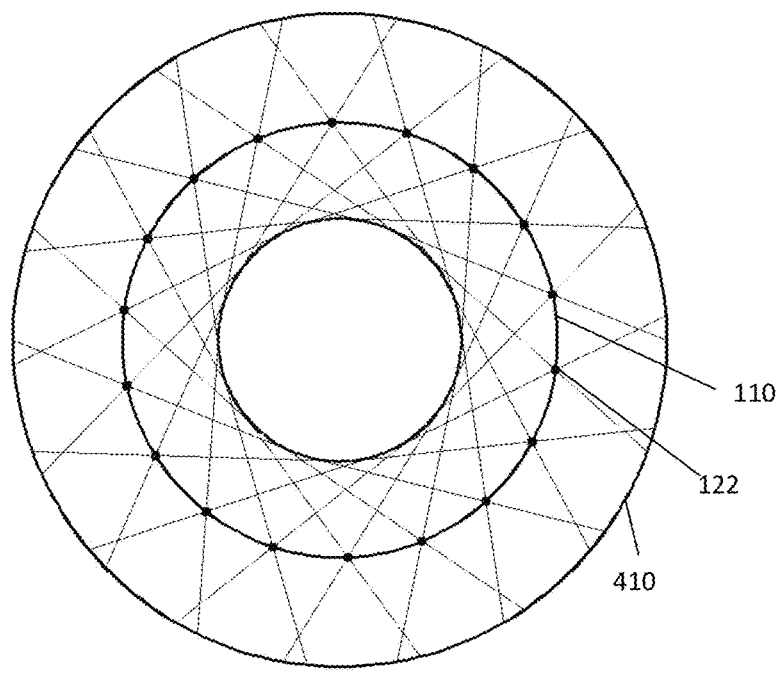
FIG. 10 illustrates a collimating aperture configuration wherein overlap is present on the detector.

As also indicated in the first aspect, according to prior art, the number of pinholes is limited by the amount of overlap allowed on the detector. FIG. 9 is an illustration of a prior art pinhole-configuration without overlap. If the radius of the collimator and the detector are not changed and more pinholes are added to the cylinder, the projections will start to overlap, as shown in FIG. 10. Overlap is often undesirable because the detections in the regions of overlap will be more ambiguous. However, a combination of overlapping and non-overlapping data can improve the reconstruction quality. According to prior art, the amount of overlap is a parameter that needs to be fixed when the collimator is designed. Nevertheless, as indicated for the first aspect, according to embodiments of the present invention, overlap can be used as a parameter and may be variable, e.g. even during imaging for the reconstruction of one and the same object. Further features and advantages of embodiments of the present invention may correspond with standard and optional features as described in the first aspect.

In a further aspect, the present invention relates to a method for imaging an object in a tomography system. The method may be especially suitable for performing single photon emission computed tomography, although embodiments are not limited thereto. The method may advantageously be performed using a collimating system as described in the first aspect or an imaging system as described in the second aspect, although embodiments of the present invention are not limited thereto. The method according to embodiments of the present invention comprises selectively and temporarily shutting at least two of a plurality of collimating apertures of a static collimator, e.g. using shutters having a shutting element for closing the collimating apertures, thereby alternatingly and temporarily opening shutters for non-neighbouring collimating apertures. The method also comprises detecting the radiation transmitted through the un-shut collimating apertures. The method further comprises correlating the detected radiation with the collimator apertures un-shut during the detecting and deriving therefrom information of the object of interest. Correlating the detected radiation with the collimator apertures un-shut during the detection typically allows for more easily and in some cases unambiguously assigning certain detections to certain collimator apertures, i.e. to certain projection angles. Deriving information of the object typically may comprise reconstructing the image based on the projections obtained. Embodiments according to the present aspect may allow for emulating a virtual rotation of the collimating system used, for example by alternatingly opening one or a group of distanced, e.g. equally distanced, collimating apertures. The method thereby may be adapted for not simultaneously opening neighbouring collimating apertures. According to some embodiments of the present invention the shutting elements also may be controlled for actively collimating radiation passing through non-shut collimating apertures.

As indicated above, the methods may be computer-implemented methods for performing a method for imaging or a method for designing a collimator system. Such a computer-implemented method may be implemented on a processing system that includes at least one programmable processor coupled to a memory subsystem that includes at least one form of memory, e.g., RAM, ROM, and so forth. It is to be noted that the processor or processors may be a general purpose, or a special purpose processor, and may be for inclusion in a device, e.g., a chip that has other components that perform other functions. Thus, one or more aspects of embodiments of the present invention can be implemented in digital electronic circuitry, or in computer hardware, firmware, software, or in combinations of them. The processor may be adapted for performing a method for designing a collimating system or for imaging an object in tomography or may comprise instructions for performing such a method. The processing system may include a storage subsystem that has at least one disk drive and/or CD-ROM drive and/or DVD drive. In some implementations, a display system, a keyboard, and a pointing device may be included as part of a user interface subsystem to provide for a user to manually input information. Ports for inputting and outputting data also may be included. More elements such as network connections, interfaces to various devices, and so forth, may be included. The various elements of the processing system may be coupled in various ways, including via a bus subsystem. The memory of the memory subsystem may at some time hold part or all of a set of instructions that when executed on the processing system implement the steps of the method embodiments described above. While a processing system as such is prior art, a system that includes the instructions to implement aspects of the methods as described above is not prior art.

The present invention also includes a computer program product that provides the functionality of any of the methods according to the present invention when executed on a computing device. Such computer program product can be tangibly embodied in a carrier medium carrying machine-readable code for execution by a programmable processor. The present invention thus relates to a carrier medium carrying a computer program product that, when executed on computing means, provides instructions for executing designing a collimator according to any of the methods as described above. The term "carrier medium" refers to any medium that participates in providing instructions to a processor for execution. Such a medium may take many forms, including but not limited to, non-volatile media, and transmission media. Non-volatile media includes, for example, optical or magnetic disks, such as a storage device that is part of mass storage. Common forms of computer readable media include, a CD-ROM, a DVD, a flexible disk or floppy disk, a tape, a memory chip or cartridge or any other medium from which a computer can read. Various forms of computer readable media may be involved in carrying one or more sequences of one or more instructions to a processor for execution. The computer program product can also be transmitted via a carrier wave in a network, such as a LAN, a WAN or the Internet. Transmission media can take the form of acoustic or light waves, such as those generated during radio wave and infrared data communications. Transmission media include coaxial cables, copper wire and fibre optics, including the wires that comprise a bus within a computer.

Figure 11:
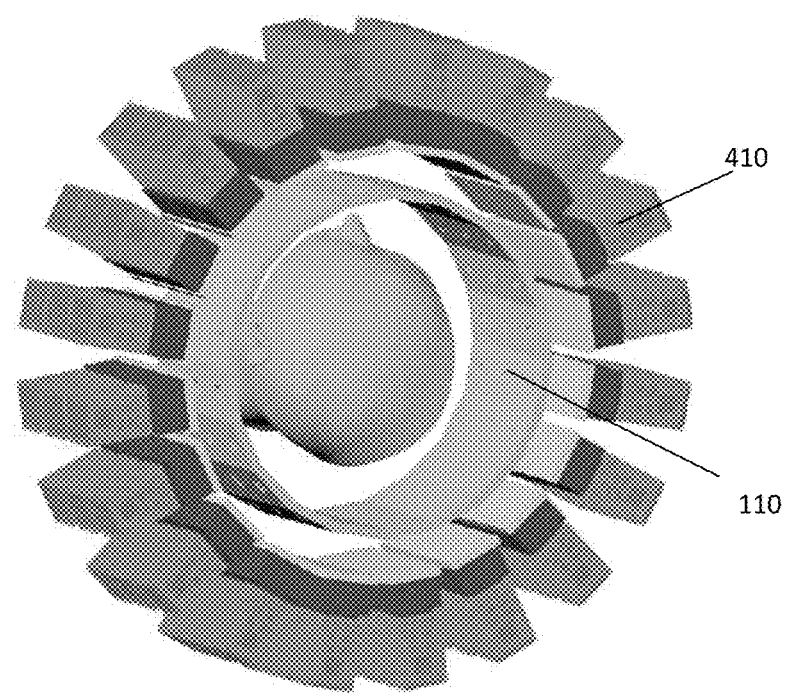
FIG. 11 illustrates a multi-pinhole brain SPECT collimator for a full-ring of gamma detector modules, according to an embodiment of the present invention.

By way of illustration, embodiments of the present invention not being limited thereto, an example is given of the design of a static full-ring multi-pinhole collimator for brain SPECT. Brain SPECT is in clinical practice mostly performed with a dual head SPECT scanner with fan beam or parallel hole collimators. The resolution of such a system is typically about 7-8 mm, which is rather poor to image the complex structures of the human brain. In small animal SPECT, sub-millimeter resolutions are obtained using multi-pinhole collimators. Using a non-rotating full-ring multi-pinhole collimator according to an embodiment of the present invention to insert in the LaPET detector ring, should allow for brain SPECT imaging with a resolution of 4 mm or better. An example of such a system is drawn in FIG. 11. A full-ring geometry allows in the present example for having complete solid angle coverage and allows for making a stationary system. This allows doing faster dynamic imaging. In the present example the collimator is designed for the LaPet system, being a PET detector ring made of 24 $LaBr_3$ detectors. It was in the present example chosen because of its very good energy resolution and its large axial FOV.

For the design of the collimator, four important specifications were to be taken into account. The first specification is that the collimator was designed for the LaPET detector ring, described for example by Kyba et al. in IEEE Nuclear Science Symposium Conference Record: pp 4123-4128 (2007). The LaPET detector ring consists of 24 LaBr3 detectors of 27 by 60 pixels, each 4×4×30 mm large. The second specification is that the Field-Of-View (FOV) must be large enough to image a full human brain, which is assumed to be a cylinder with a radius of 110 mm and an axial length of 125 mm. The third specification is that the collimator must not rotate. The fourth specification is that the system must have a resolution of 4 mm or better.

Figure 12:
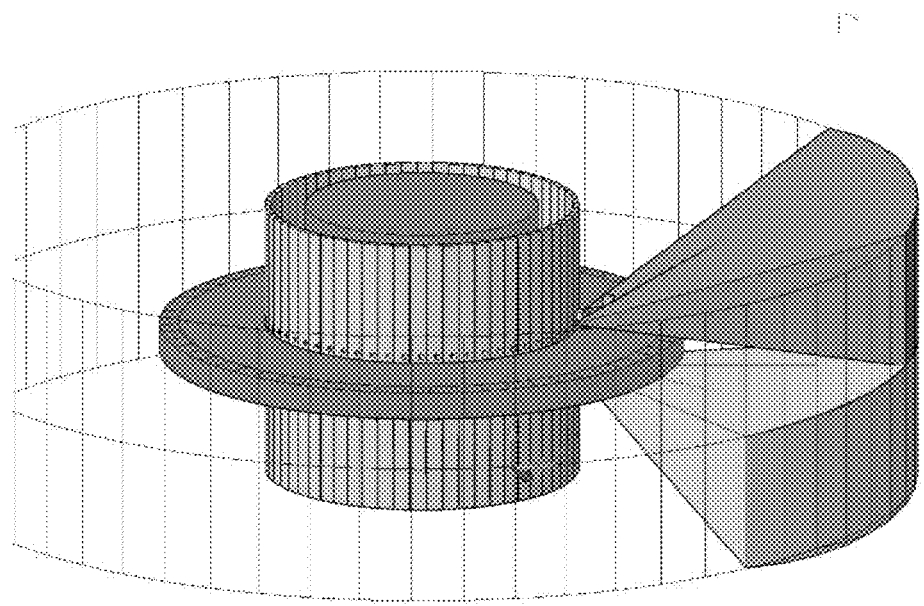
FIG. 12 illustrates a general design of a collimator according to an embodiment of the present invention.

One design that is compliant with all specifications is shown in FIG. 12. The tungsten collimator has a radius of 145 mm and has two rings of 64 pinholes with a diameter of 2 mm. The rings are spaced 8.12 mm apart. The pinholes on the inferior ring see the superior part of the brain. The pinholes on the superior ring see the inferior part of the brain. An annulus is placed between the two pinhole-rings to prevent the projections from overlapping in the axial direction. Each pinhole sees half of the transaxial FOV.

Given the specifications of the FOV and the properties of the LaPET detector, a maximum of 16 pinholes (8 in each ring) can simultaneously project on the detector without causing overlap. Therefore, the pinholes are equipped with collimating shutters. The shutter blocks all radiation when moved in front of a pinhole. A sequence of shutter movements is then performed to obtain an acquisition setup that simulates a rotational movement. A shutter also has a collimating element that is used to prevent the projection of the neighboring pinhole on one side from overlapping with the projection of the open pinhole on the other side.

All simulations and reconstructions were based on ray-tracing and analytical calculations. In a first simulation, the sensitivity is calculated at each point in the FOV. Also, the mean sensitivity over a cylinder with a radius of 110 mm and a length of 125 mm is calculated. The calculations were based on the formula proposed by Mallard and Myers in Phys. Med. Biol. 8 pp 165-182 (1963). To investigate penetration through the pinhole, the mean sensitivity was also calculated with the effective pinhole diameter ($d_{se}$) as proposed by Paix in Phys. Med. Biol. 12 pp 489-500 (1967).

$$S = \frac{d_{se}^2 \sin^3 \theta}{16 b^2} \text{ with } d_{se} = \sqrt{d\left(d + \frac{2}{\mu}\tan\frac{\alpha}{2}\right) + \frac{2}{\mu^2}\tan^2\frac{\alpha}{2}}$$

with θ the incident angle measured from the plane of the pinhole, with $d_c$ the perpendicular distance from the point in the FOV to the pinhole, with μ the attenuation coefficient of tungsten and with α the openingsangle of the pinhole.

In a second simulation, the resolution is calculated at each point in the FOV. The calculations are based on the formula proposed by Anger in Radioisotope cameras Instrumentation in Nuclear Medicine vol 1, pp 485-552 (1967) and the resolution effective diameter as proposed by Accorsi in IEEE Trans. Med. Imaging 23 pp 750-763 (2004). The resolution effective diameter depends on the direction of incidence on the pinhole plane. Therefore, there are two resolution values, one for each direction. If the plane X=0 is defined by the normal to the detector plane and the vector from the pinhole to the voxel, then the parallel direction is along the y axis and the perpendicular direction is along the x axis.

$$R = \sqrt{\frac{R_i^2}{M^2} + \left(d_{re}\left(1 + \frac{1}{M}\right)\right)^2} \text{ with } M = \frac{h}{b}$$

$$d_{re\parallel} = d + \frac{\ln 2}{\mu}\left(\tan^2\frac{\alpha}{2} - \cot^2\theta\right)\cot\frac{\alpha}{2}\sin\theta$$

$$d_{re\perp} = \sqrt{\left(d + \frac{\ln 2}{\mu}\tan\frac{\alpha}{2}\sin\theta\right)^2 - \left(\frac{\ln 2}{\mu}\right)^2\cos^2\theta}$$

with h the distance between the detector and the pinhole.

Finally, a Defrise phantom is modeled using a grid with 0.5×0.5×0.5 mm voxels. The phantom has a radius of 110 mm and an axial length of 120 mm with 15 disks of 4 mm. The phantom is projected using a ray-tracer. The projections are then reconstructed using software OSEM to investigate data-completeness. 5 iterations and 8 subsets are used. The bed is axially shifted during acquisition (8.12 mm steps are used). The reconstructed image has 2×2×2 mm voxels.

Figure 13:
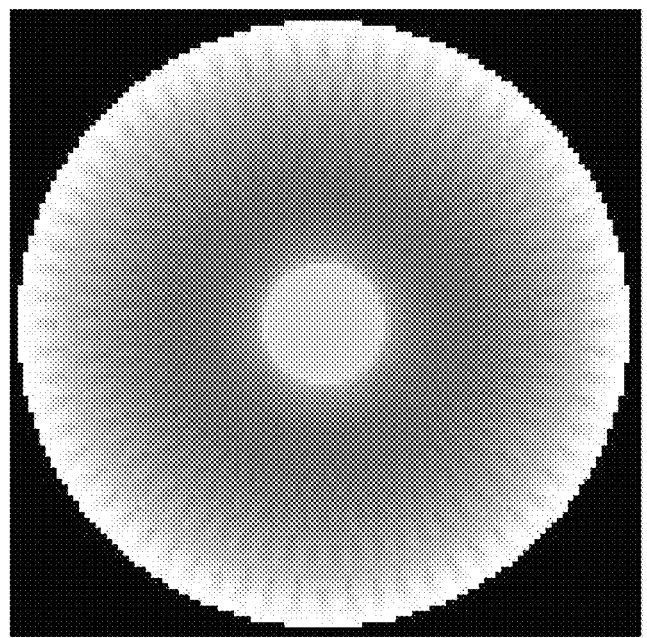
FIG. 13 illustrates the sensitivity of a central slice using a collimator according to an embodiment of the present invention.
Figure 14:
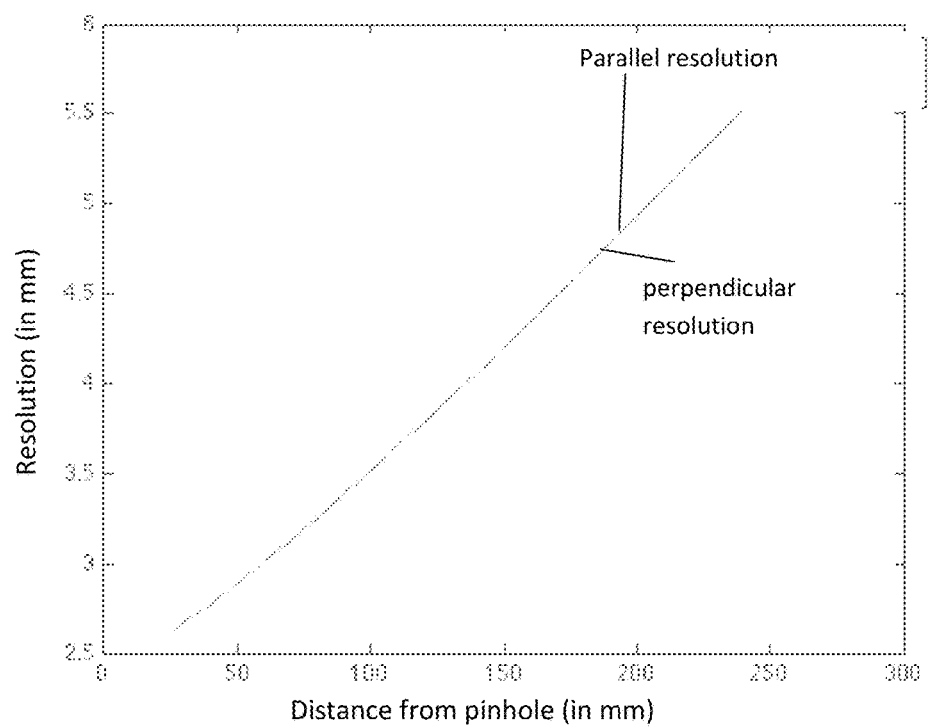
FIG. 14 illustrates a resolution simulation according to an embodiment of the present invention.
Figure 15:
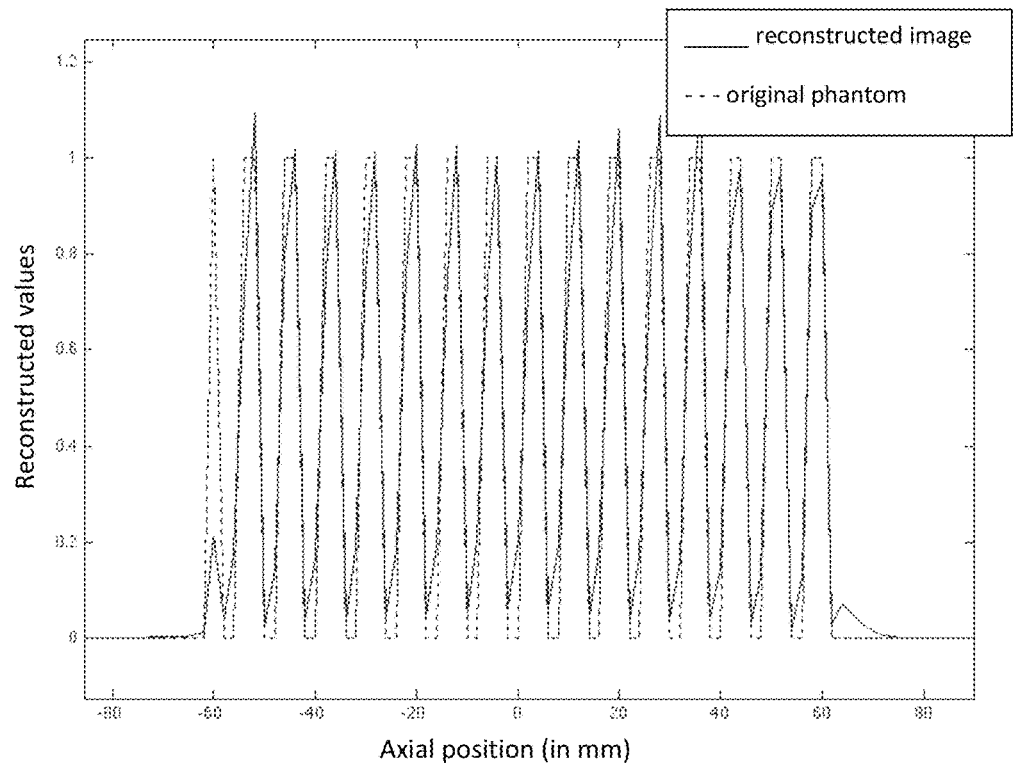
FIG. 15 illustrates a line profile of the reconstructed Defrise phantom based on simulation details according to an embodiment of the present invention, indicating good agreement with the original phantom.

The result of the sensitivity simulation for the central slice is shown in FIG. 13. The sensitivity in the center of the FOV is 1.52e-04. The mean sensitivity of the whole FOV is 5.39-05. When penetration is modeled, the sensitivity in the center of the FOV is 2.64e-04 and the mean sensitivity is 9.40e-05. In other words, 38% of the total sensitivity is due to knife-edge penetration. This is a relatively large amount but it can be modeled and included in the reconstruction algorithm and thus should not pose any problems. The result of the resolution simulation in the central slice at different distances from the pinhole is shown in FIG. 14. The resolution in the parallel direction is very similar to the resolution in the perpendicular direction. In the center of the FOV it is 4.07 mm in the parallel direction and 4.12 mm in the perpendicular direction. An axial line profile of the reconstruction Defrise phantom shows very good agreement with the original phantom, as shown in FIG. 15.

Figure 17:
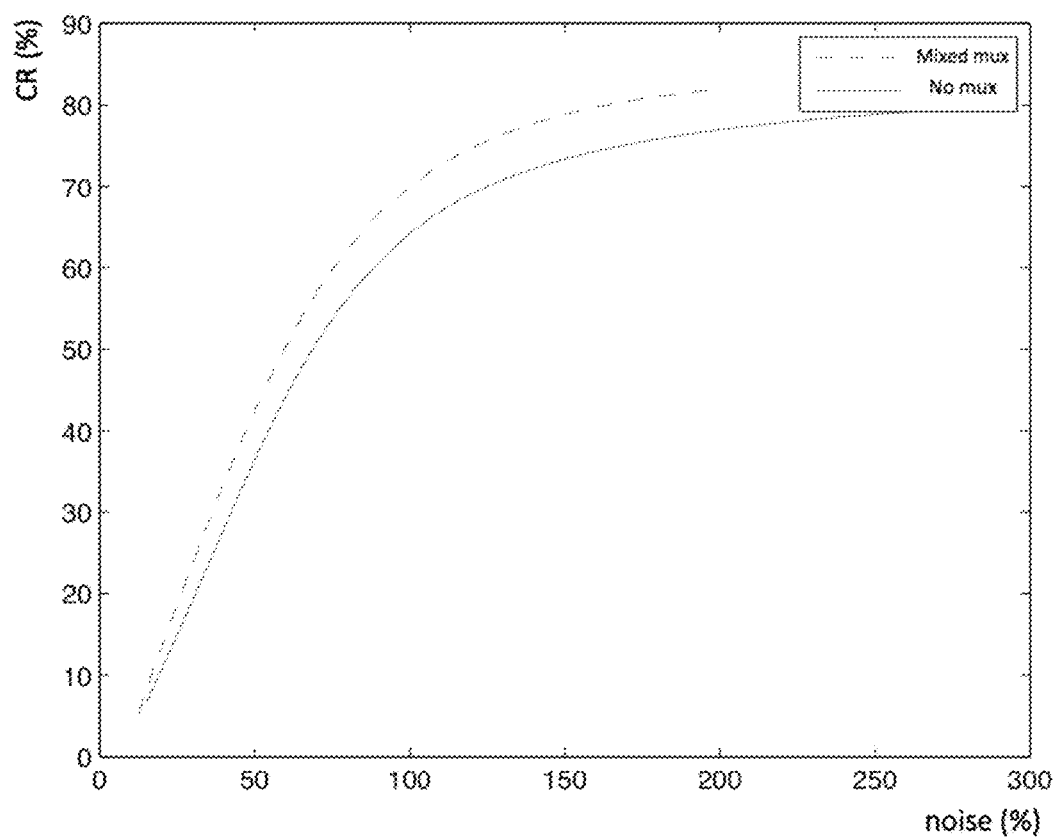
FIG. 17 shows the Contrast-Recovery-Curves for a setup without overlap compared to a setup with overlapping and non-overlapping parts.

From the above simulation results, it can be seen that the resolution of a system according to embodiments of the present invention potentially can be significantly higher than using known systems. FIG. 17 shows the potential of combining overlapping and non-overlapping data to improve image quality of a multi-pinhole brain SPECT system. The system used is the same one as described in the previous example, except for the pinhole diameter, which was 3.9 mm instead of 2 mm. Projection data of a contrast phantom with 5 hot sources (7:1) for 3 different setups were obtained: without overlap (8 pinholes are opened simultaneously), with 100% overlap (16 pinholes are opened simultaneously) and with mixed overlapping and non-overlapping data (during 20% of the scan time only 8 pinholes were opened simultaneously and during the other 80% of the scan time 16 pinholes were opened simultaneously). The projection data were simulated using a ray tracer (Siddon) and Poisson noise was added afterwards. Assumption was made of 3 million counts in the projection data for the setup without overlap. The images were reconstructed using OSEM. Compared to the reconstruction from non-overlapping data, the reconstructed images with only overlapping data showed severe artifacts. These were reduced by mixing non-overlapping and overlapping data and were completely eliminated by adding body contouring. Body contouring is the initialization of the starting image of the reconstruction algorithm with an image that is zero outside and 1 inside the contours of the object. To define the body contour, a reconstruction was performed using only the non-multiplexed data (17 iterations). The body contour was defined by thresholding the resulting image and the reconstruction was then restarted using all the data and the body contour as starting image. Image quality was assessed using Contrast-Recovery-Curves (CRC) for the reconstructed contrast phantom using (a) only non-overlapping data and body contouring and (b) mixed overlapping and non-overlapping data and body contouring. These CRC curves are shown in FIG. 17, the curve for non-overlapping data shown in solid line, and the curve for mixed overlapping and non-overlapping data shown in dashed line. After each iteration we measured the noise and the mean contrast recovery (CR) (averaged over the 5 hot sources). A 5% improvement in contrast recovery was obtained compared to the setup without overlap at 58% noise. While the invention has been illustrated and described in detail in the drawings and foregoing description, such illustration and description are to be considered illustrative or exemplary and not restrictive. The invention is not limited to the disclosed embodiments.

The foregoing description details certain embodiments of the invention. It will be appreciated, however, that no matter how detailed the foregoing appears in text, the invention may be practiced in many ways, and is therefore not limited to the embodiments disclosed. It should be noted that the use of particular terminology when describing certain features or aspects of the invention should not be taken to imply that the terminology is being re-defined herein to be restricted to include any specific characteristics of the features or aspects of the invention with which that terminology is associated.

The invention claimed is:

1. A collimating system for collimating radiation received under different angles for performing tomography, the collimating system comprising:
   a static collimator including a plurality of collimating apertures, and shutters for selectively and temporarily shutting at least two of said collimating apertures;
   wherein the shutters have a shutting element for closing said at least two collimating apertures;
   wherein the collimating system further comprises at least one collimating element distinct from the shutting element for collimating radiation passing through non-shut collimating apertures in a direction so as to prevent overlap between radiation stemming from different non-shut collimating apertures.

2. The collimating system according to claim 1, wherein the static collimator is at least partially ring-shaped and wherein the plurality of collimating apertures is positioned on a same collimator ring.

3. The collimating system according to claim 1, wherein the at least one collimating element is part of one of the shutters.

4. The collimating system according to claim 3, wherein the one of the shutters has a shutting element for shutting a predetermined collimating aperture and the at least one collimating element is shaped for controlling collimation of radiation passing through a collimating aperture neighboring the predetermined collimating aperture.

5. The collimating system according to claim 3, wherein the at least one collimating element comprises a slanted surface of the one of the shutters.

6. The collimating system according to claim 1, wherein the at least one collimating element is part of an additional collimator configured with respect to the static collimator for controlling overlap between radiation stemming from different non-shut collimating apertures.

7. The collimating system according to claim 1, wherein the collimating system comprises a controller programmed for controlling the shutters for opening the collimating apertures in a predetermined manner.

8. The collimating system according to claim 7, wherein the controller is programmed for controlling the shutting elements and the corresponding at least one collimating element to move simultaneously.

9. The collimating system according to claim 7, wherein the controller is programmed for controlling at least a subset of the shutters individually.

10. The collimating according to claim 7, wherein the controller is programmed for alternatingly and temporarily opening the shutting elements for collimating apertures.

11. The collimating system according to claim 7, wherein the controller is programmed for alternatingly and temporarily opening the shutting elements for a subset of collimating apertures such that over a predetermined time period, all collimating apertures have been un-shut.

12. The collimating system according to claim 1, wherein the collimator is ring shaped and for use with a ring shaped detector and wherein the number of apertures fulfills the following equation:

$$\text{number of apertures} > \frac{\pi}{a\cos\left(\frac{R_{FOV}}{R_d}\right) - a\cos\left(\frac{R_{FOV}}{R_c}\right)}$$

wherein Rd is the radius of the detector, Rc is the radius of the static collimator and RFOV is the transaxional field-of-view radius.

13. An imaging system comprising a detector, a collimating system according to claim 1, and a correlator for correlating signals detected using the detector with collimated apertures un-shut at the moment of detection.

14. The collimating system according to claim 1, wherein the shutting element is formed from a radiation-blocking material, and the at least one collimating element extends from the shutting element at an angle transverse to the shutting element.

15. The collimating system according to claim 1, wherein the shutting elements arranged between the at least one collimating element and the static collimator.

16. The collimating system according to claim 1, wherein the at least one collimating element is coupled to the shutting element.

17. The collimating system according to claim 1, wherein the static collimator, at least one collimating element, and the shutting elements are arranged concentrically, and the at least one collimating element is arranged between the static collimator and the shutting elements.

18. A method for imaging an object, the method comprising the steps of:
selectively and temporarily shutting at least two of a plurality of collimating apertures of a static collimator using shutters having a shutting element for closing said at least two collimating apertures, thereby alternatingly and temporarily opening shutting elements for collimating apertures or subsets of collimating apertures;
detecting the radiation transmitted through non-shut collimating apertures;
correlating the detected radiation with the non-shut collimator apertures during the detecting;
deriving therefrom information of the object of interest, and
using collimating elements for collimating radiation passing through the non-shut collimating apertures in a direction so as to prevent overlap between radiation stemming from different non-shut collimating apertures.

19. The method according to claim 18, wherein the step of selectively and temporarily shutting comprises shutting the shutting element having a thickness of at least 0.5 mm over its shutting area for blocking radiation stemming from the object of interest passing through the collimating apertures.

20. A collimating system for collimating radiation received under different angles for performing tomography, the collimating system comprising:
a static collimator defining a plurality of collimating apertures;
a plurality of shutters, each of the shutters configured to selectively and temporarily shut at least two of said collimating apertures, each of the shutters including a shutting element that blocks said at least two collimating apertures; and
at least one collimating element that collimates radiation that passes through non-blocked collimating apertures in a direction that prevents overlap between radiation stemming from different non-shut collimating apertures,
wherein the static collimator is provided on a first side of the shutting element and the at least one collimating element is provided on a second side of the shutting element, the first side of the shutting element being opposite from the second side of the shutting element.

* * * * *